US008303302B2

(12) United States Patent
Teasdale

(10) Patent No.: US 8,303,302 B2
(45) Date of Patent: Nov. 6, 2012

(54) SYSTEMS AND METHODS FOR ORTHODONTIC DEVICES

(76) Inventor: Russell C. Teasdale, Portland, OR (US)

( * ) Notice: Subject to any disclaimer, the term of this patent is extended or adjusted under 35 U.S.C. 154(b) by 0 days.

(21) Appl. No.: 12/899,514

(22) Filed: Oct. 6, 2010

(65) Prior Publication Data

US 2011/0244413 A1 Oct. 6, 2011

Related U.S. Application Data

(63) Continuation of application No. PCT/US2009/064494, filed on Nov. 15, 2009.

(60) Provisional application No. 61/224,511, filed on Jul. 10, 2009.

(51) Int. Cl.
*A61C 19/00* (2006.01)

(52) U.S. Cl. ................................ 433/34; 433/6; 433/37

(58) Field of Classification Search .................. 433/2–3, 433/5–6, 18, 22, 24, 34, 36–38, 45, 229; 264/16–20

See application file for complete search history.

(56) References Cited

U.S. PATENT DOCUMENTS 4,368,040 A * 1/1983 Weissman ...................... 433/36
4,657,508 A 4/1987 Dellinger
4,872,936 A * 10/1989 Engelbrecht ............... 156/307.3
4,932,866 A * 6/1990 Guis ............................... 433/24
5,711,665 A * 1/1998 Adam et al. ...................... 433/9
5,975,893 A 11/1999 Chishti et al.
7,125,248 B2 10/2006 Phan et al.
2003/0190575 A1* 10/2003 Hilliard ............................ 433/6
2007/0087302 A1* 4/2007 Reising et al. .................. 433/24
2007/0238066 A1* 10/2007 Kopelman et al. .............. 433/24
2009/0029320 A1 1/2009 Auderset et al.

FOREIGN PATENT DOCUMENTS

KR 10-2007-0121714 A 12/2007
WO 2006/105684 A1 10/2006

OTHER PUBLICATIONS

File wrapper for parent application PCT/US2009/064494, not yet published.
Int'l Search Report and Written Opinion for PCT/US2009/064494.

* cited by examiner

*Primary Examiner* — Cris L Rodriguez
*Assistant Examiner* — Edward Moran
(74) *Attorney, Agent, or Firm* — Silicon Forest Patent Group; Paul J. Fordenbacher, Esq

(57) ABSTRACT

Embodiments presented herein provide apparatus and methods for forming and coupling an attachment device onto one or more teeth. A system comprises a template including a shell having a cavity defining a shape that is operable to receive one or more teeth. The template comprises an aperture at one or more predetermined locations. The aperture defines an aperture perimeter. The system further comprises one or more attachment molds. Each attachment mold comprises a mold bore therethrough. The attachment mold further includes a mold perimeter surface that defines a predetermined shape, wherein each of the aperture perimeters being operable to receive and cooperate with the mold perimeter surface of one of the attachment molds. Each mold bore being operable for providing a mold for forming an attachment device coupled to a tooth of a desired shape and orientation from curable material that may be disposed within the mold bore.

37 Claims, 8 Drawing Sheets

100 300 310 200 5 206 210 5 212 204 202 154 150 150

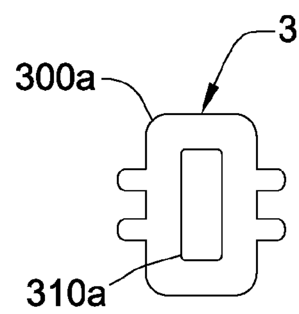
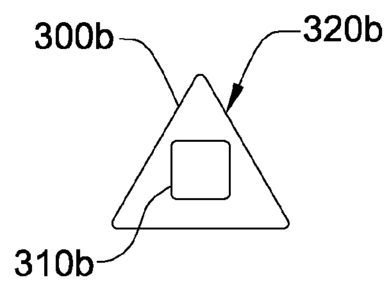
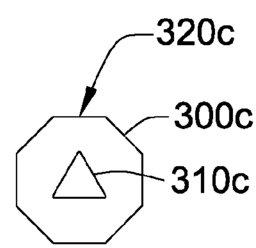
FIG. 7A FIG. 7B FIG. 7C
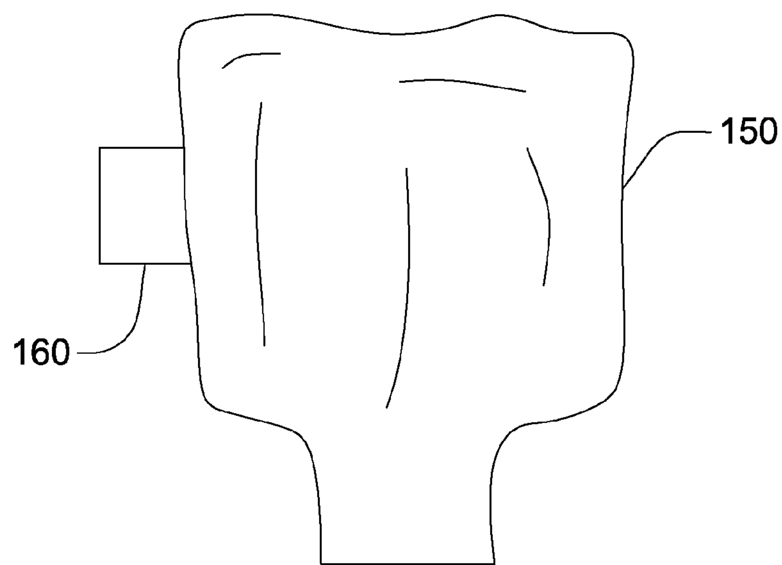
FIG. 9

SYSTEMS AND METHODS FOR ORTHODONTIC DEVICES

RELATED APPLICATIONS

This application is a continuation of and claims priority to PCT patent application Serial Number PCT/US09/64494, filed Nov. 15, 2009, entitled SYSTEMS AND METHODS FOR ORTHODONTIC DEVICES, incorporated herein in its entirety by reference, which is a non-provisional application claiming the benefit of U.S. Provisional Application No. 61/224,511, filed Jul. 10, 2009, incorporated herein in its entirety by reference.

FIELD

The present invention is related generally to the field of orthodontics. More particularly, the present invention involves systems and methods that enable accurate formation and placement of composite attachments on a dental surface for a patient undergoing orthodontic treatment.

BACKGROUND

Orthodontic treatment involves the repositioning of misaligned teeth and improving bite configurations for improved dental function and cosmetic appearance. Repositioning teeth may be accomplished by applying controlled forces to the teeth over an extended period of time. A number of systems and techniques are known for applying the required forces to the teeth.

One known method for applying forces to the teeth is by the use of elastic positioning appliances as described by Chishti et al. in U.S. Pat. No. 5,975,893. Such positioning appliances comprise a thin shell of elastic material that generally conforms to a patient's teeth but is slightly out of alignment with the initial tooth position. Placement of the positioning appliance over the teeth applies controlled forces to the teeth to gradually move the teeth into a new position. Repetition of this process with successive positioning appliances comprising new teeth positions eventually moves the teeth through a series of intermediate positions to a final desired position.

When the positioning appliance is placed over a prescribed group of teeth, one or more of the teeth may provide an anchor for holding the appliance in place while the stiffness of the appliance imparts a positioning force against at least a portion of the target teeth.

The anchoring and repositioning abilities of positioning appliances are dependent at least in part on the physical features and positions of the patient's teeth, previous dental work, and the like. Among other things, these physical features may not be optimally suitable for providing an optimal force bearing surface for anchoring or applying positioning forces to the teeth by the positioning appliance. For example, but not limited thereto, positioning appliances may have difficulty applying certain forces to individual teeth, such as extrusive forces (e.g., pulling or raising a tooth relative to the jaw).

Attempts to augment the force transfer between the positioning appliance and the teeth have been attempted, such as those described by Phan et al. in U.S. Pat. No. 7,125,248. Phan et al. describes the use of attachment devices that are bonded to one or more teeth or other dental feature so as to provide an enhanced surface upon which the positioning appliance may bear. Phan et al. describes a method of forming and bonding the attachment device to the teeth with the use of a mold. The mold is substantially in the form of the positioning appliance, which substantially conforms to the teeth, but has one or more negative impressions having a shape that is complementary to the desired attachment device. Malleable polymerizing material is placed in the negative impression and the mold slidingly received over the teeth. The polymerizing material is cured such that when the mold is removed from the teeth, the now polymerized material forms the attachment device that, if successful, is bonded to the tooth. This method is referred herein as the mold-in-place approach.

In practice, the mold-in-place approach as provided by Phan et al. has a number of shortcomings. One shortcoming, among others, is that a precise amount of the polymerizing material must be disposed within the respective negative impression otherwise the negative impression may be underfilled or overfilled. An underfilled negative impression may lead to, among other things, an underdeveloped or malformed attachment device that is not suitable for the intended purpose. Further, an underfilled negative impression may lead to, among other things, the polymerizing material making only partial or insufficient contact with the tooth surface thereby resulting in an attachment device that is partially or insufficiently bonded to the tooth. Ensuring full contact between the polymerizing material and the tooth surface is further complicated by the necessity of using a very viscous polymerizing material. The polymerizing material must be very viscous so that, among other things, the polymerizing material stays substantially within the negative impression during handling of the mold and in placement on the teeth. Being very viscous or putty-like, the polymerizing material may not flow towards the tooth surface and make full contact therewith prior to curing resulting in a poorly or not bonded attachment device.

An overfilled negative impression may lead to, among other things, an ill-fitting, distorted mold. An overfilled mold may, among other things, not seat properly on the tooth surface so as to not position the polymerizing material at the intended location and/or may form a malformed attachment device after cure. The mold may have to be forcibly held in place on the teeth to ensure that it is properly seated thereon during the curing process.

An overfilled negative impression may lead to, among other things, flashing. Flashing is excess polymerizing material that may deposit on unintended tooth surfaces and/or beyond the prescribed footprint of the attachment device. The excess material may be unintentionally deposited on the tooth surface when the mold is slidingly received onto the teeth. The excess material may extrude away from the negative impression when pressure is exerted onto the mold during placement and cure of the polymerizing material. Flashing must be removed to allow for proper placement of the positioning appliance onto the teeth. Flashing has the potential to cause, among other things, the positioning appliance to not seat properly on the teeth and may cause unintentional forces on the teeth resulting in improper repositioning. Removing flashing is labor and time intensive and may lead to damage to the resulting attachment device and/or undesirable modification of the underlying tooth surface to which it is attached.

A precisely formed attachment device is crucial for optimal performance of the positioning appliance. The shape of the positioning appliance is designed taking into account the precise position and shape of any attachment devices that may be provided. A malformed or misplaced attachment device may lead to, among other things, a malfitting positioning appliance that may result in non-prescribed or inefficient expressions of intended forces acting on one or more teeth resulting in unpredictable and undesired repositioning of the teeth.

The consequences of improperly formed attachment devices may lead to an interruption in the proposed intended sequence of progressive positioning appliances. Positioning appliances are created and supplied by the manufacturer as a set with the expectation that the attachment devices are properly formed. In many cases, the imprecise placement and formation of the attachment devices results in, among other things, inappropriate repositioning of the teeth prolonging the treatment, and requiring the manufacture of additional positioning appliances to reposition or fine-tune the repositioning of the teeth which increases the cost of materials and patient and doctor time.

It would therefore be desirable to provide apparatus and methods for forming and positioning attachment devices that address one or more of these shortcomings.

SUMMARY

Embodiments of the present invention provide apparatus and methods for simultaneously forming and coupling an attachment device onto one or more teeth. In accordance with an embodiment, a system is provided that comprises a template including a shell having a cavity defining a shape that is operable to receive one or more teeth. The template includes a template inner surface and a template outer surface opposite the template inner surface. The template further comprises an aperture at one or more predetermined locations that extends from the template inner surface to the template outer surface therethrough. The aperture defines an aperture perimeter having a predetermined shape. The system further comprises one or more attachment molds. Each attachment mold comprises a mold first surface and a mold second surface opposite the mold first surface. The attachment mold includes a mold bore having a bore surface extending from the mold first surface to the mold second surface therethrough. The attachment mold further includes a mold perimeter surface that defines a predetermined shape, wherein each of the aperture perimeters being operable to receive and cooperate with the mold perimeter surface of one of the attachment molds. Each mold bore is operable for providing a mold for forming an attachment device of a desired shape and orientation from curable material that couples to the tooth that may be disposed within the mold bore.

In accordance with an embodiment, a method for simultaneously forming and coupling an attachment device on one or more teeth is provided. The method comprises providing a template including a prescribed number and placement of apertures; disposing the template over the teeth exposing tooth surface through each aperture; disposing an attachment mold through each respective aperture, wherein the attachment mold includes a mold bore suitable for providing a mold for forming an attachment device of the desired shape from curable material; removably coupling the mold first surface of the attachment mold to the exposed tooth surface with the mold bore defining target tooth surface; preparing the target tooth surface to receive curable material; disposing curable material within the mold bore and in contact with the target tooth surface; curing the curable material to a hardened state to form an attachment device that is coupled to the target tooth surface; removing the template; and removing the attachment mold from the attachment device.

BRIEF DESCRIPTION OF THE DRAWINGS

Embodiments are illustrated by way of example and not by way of limitation in the figures of the accompanying drawings, in which like references may indicate similar elements throughout the various figures unless otherwise specified.

FIG. 7A is a top view of an attachment mold in accordance with an embodiment;

FIG. 7B is a top view of an attachment mold in accordance with another embodiment;

FIG. 7C is a top view of an attachment mold in accordance with yet another embodiment;

FIG. 9 is a side view of the attachment device as coupled to the tooth, in accordance with an embodiment;

DETAILED DESCRIPTION

Figure 1:
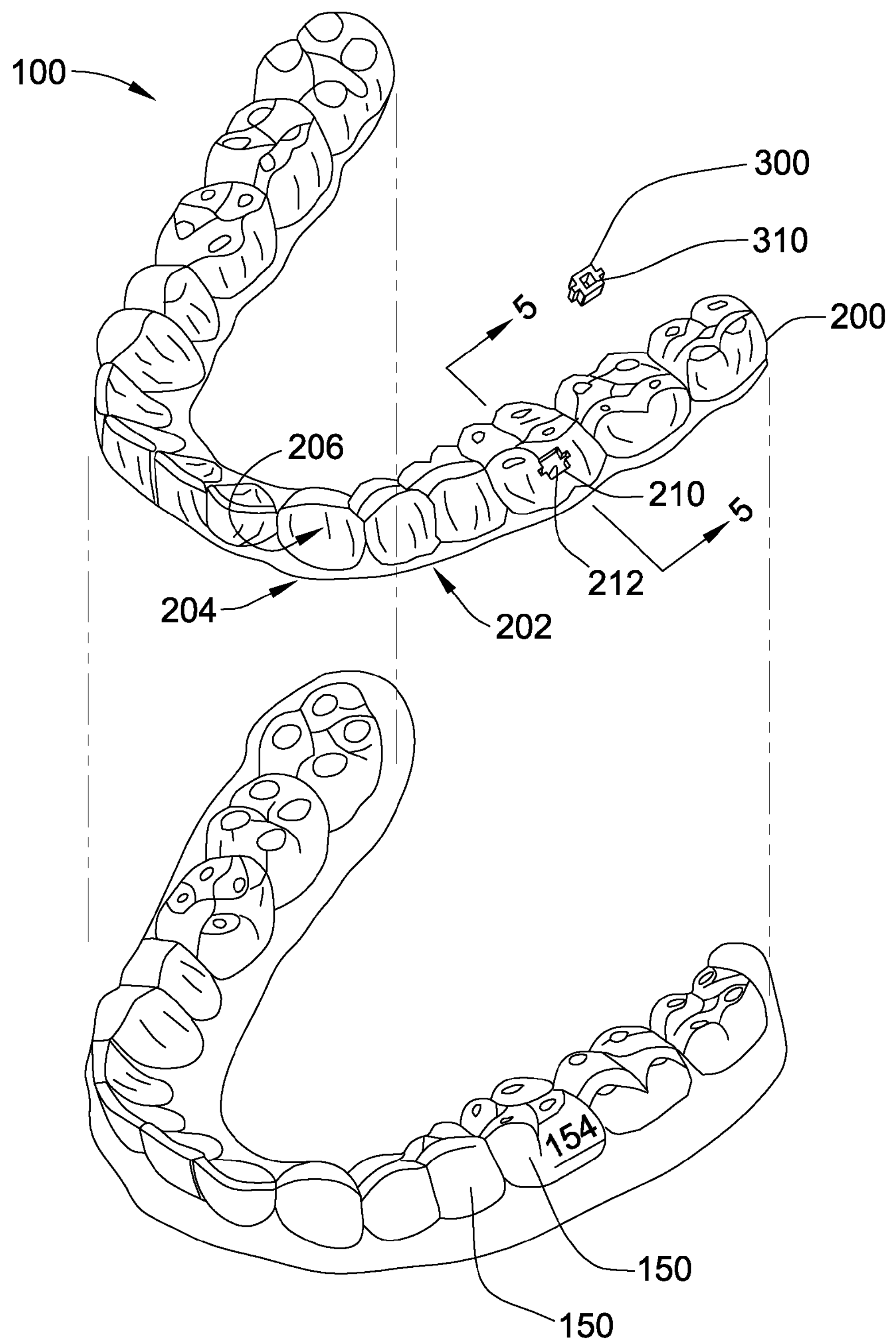
FIG. 1 is a perspective view of a system for forming and coupling one or more attachment devices onto one or more teeth, in accordance with an embodiment.

In the following description, embodiments of apparatus and methods will be disclosed. For purposes of explanation, specific numbers, materials, and/or configurations are set forth in order to provide a thorough understanding of the embodiments. However, it will also be apparent to those skilled in the art that the embodiments may be practiced without one or more of the specific details, or with other approaches, materials, components, etc. In other instances, well-known structures, materials, and/or operations are not shown and/or described in detail to avoid obscuring the embodiments. Accordingly, in some instances, features are omitted and/or simplified in order to not obscure the disclosed embodiments. Furthermore, it is understood that the embodiments shown in the figures are illustrative representations and are not necessarily drawn to scale.

Reference throughout this specification to "one embodiment" or "an embodiment" means that a particular feature, structure, or characteristic described in connection with the embodiment is included in at least one embodiment of claimed subject matter. Thus, the appearances of the phrase "in one embodiment" or "an embodiment" in various places throughout this specification are not necessarily all referring to the same embodiment. Furthermore, the particular features, structures, or characteristics may be combined in one or more embodiments.

Reference will now be made to embodiments illustrated in the drawings and specific language which will be used to describe the same. It will nevertheless be understood that no limitation of the scope of the invention is thereby intended. Alterations and further modifications of the illustrated embodiments and further applications of the principles of the invention, as would normally occur to one skilled in the art to which the invention relates, are also within the scope of the invention.

For the purposes of the subject matter disclosed herein, reference to a positioning appliance refers to an appliance, such as, but not limited to, a polymeric shell, having cavities with geometries shaped to receive and resiliently reposition from one position to a successive position of one or more teeth, such as, but not limited to, appliances provided in Chishti et al., U.S. Pat. No. 5,975,893.

For the purposes of the subject matter disclosed herein, reference to an attachment device refers to an element having predetermined dimensions which is coupled to a tooth or restored tooth surface and operable to be engaged by a positioning appliance to enhance the ability of the positioning appliance to exert a controlled orthodontic force on one or more teeth and/or to increase the retention of the positioning appliance on the teeth.

For the purposes of the subject matter disclosed herein, reference to flash and flashing refers to excess curable material, such as, but not limited to, polymerizing material, that may be deposited on the tooth surface during the molding of the attachment device.

Figure 2:
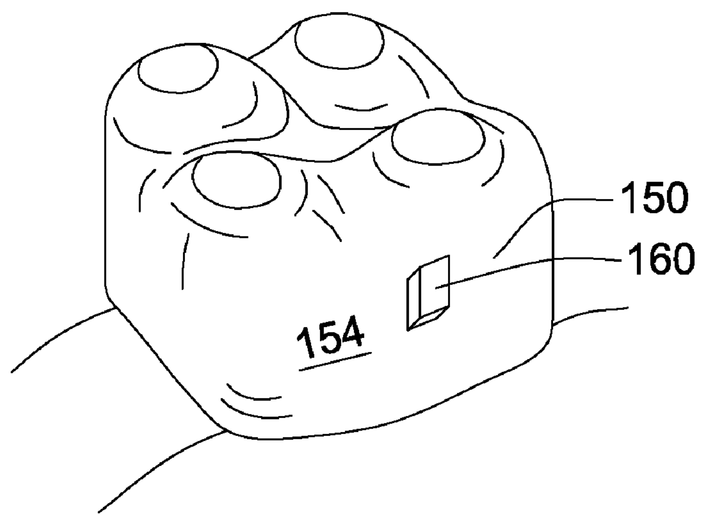
FIG. 2 is a perspective view of an attachment device coupled to a tooth, in accordance with an embodiment.

FIG. 1 is a perspective view of a system 100 for simultaneously forming and coupling attachment devices onto one or more teeth 150, in accordance with an embodiment. FIG. 2 is a perspective view of an attachment device 160 coupled to a tooth 150, in accordance with an embodiment. In FIG. 1, the system 100 comprises a template 200 and one or more attachment molds 300. The template 200 comprises a shell having a cavity 202 with a shape operable to receive one or more teeth 150. The template 200 defines a template inner surface 204 and a template outer surface 206 opposite the template inner surface 204. The template 200 is operable to removably engage the teeth 150.

At one or more predetermined locations the template 200 comprises an aperture 210 that extends from the template inner surface 204 to the template outer surface 206 therethrough. The aperture 210 defines an aperture perimeter 212 that is operable to receive and cooperate with the mold perimeter surface 320 of one of the attachment molds 300 as will be described below.

The predetermined location of each of the apertures 210 is determined by the prescribed location of a desired attachment device on a tooth surface. The location of the desired attachment device is determined and prescribed, at least in part, by the dentist in accordance with a treatment plan. As will be discussed below, each aperture 210 is operable to receive and cooperate with an attachment mold 300 therein such that the attachment device may be formed and located at the prescribed location and orientation on a tooth surface. Discussion of the process for determining the prescribed location of the desired attachment device is provided below.

The template 200 may further comprise handling structures and surfaces to assist in the placement and removal of the template 200 from the teeth 150, in accordance with another embodiment. The template 200 may incorporate frangible portions to allow for the tearing away or dividing of the template 200 into pieces to assist in removing the template from the teeth 150, in accordance with another embodiment.

The template 200 may, but not necessarily, fit over all teeth 150 present in the upper or lower jaw. In accordance with an embodiment, the template 200 is operable to fit over one or more teeth 150, one or more of which is to receive an attachment device 160. In accordance with an embodiment, the template 200 is operable to fit over one tooth 150 which is to receive an attachment device 160.

The teeth 150 adjacent to those to receive an attachment device 160 may be used to provide a base or anchor region for holding the template 200 in place as it locates respective apertures 210 in the desired locations of teeth 150 to receive an attachment device 160. In accordance with an embodiment, the template inner surface 204 sufficiently conforms to the contours of the teeth 150 such that the template 200 snaps into place and is removably coupled to the teeth 150. In another embodiment, the template 200 is manually held in place during placement onto the teeth 150 and cure of the curable material.

In accordance with an embodiment, the template 200 comprises a thin polymeric material. The template 200 may comprise any suitable material and be fabricated using any suitable process. In accordance with an embodiment, the template 200 of FIG. 1 may be formed from a thin sheet of a suitable elastomeric polymer, such as Tru-Tain thermal forming dental material, Tru-Tain Plastics, Rochester, Minn. 55902, which may be formed over a replica of the teeth. In other embodiments, the template 200 may be formed using additive manufacturing technology, also known as rapid prototyping, in which the template 200 is produced from a base material directly from computer aided design software. It is appreciated that many fabrication processes may be suitable for fabricating the template 200 and not limited to the examples presented herein.

Figure 3:
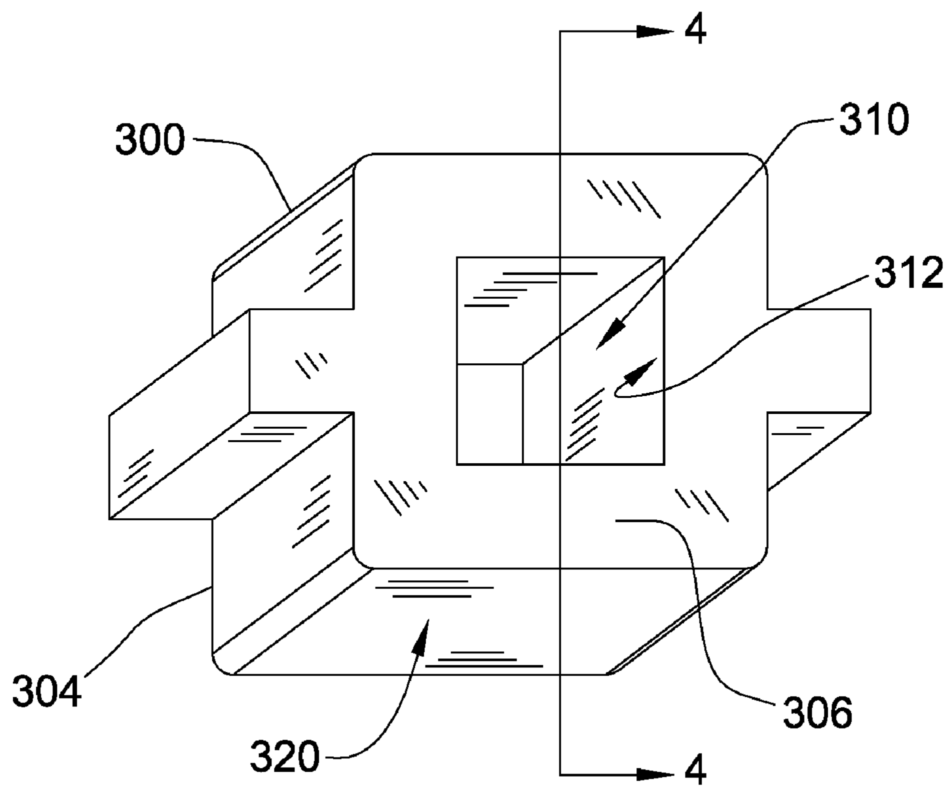
FIG. 3 is a perspective view of an attachment mold, in accordance with an embodiment.
Figure 4:
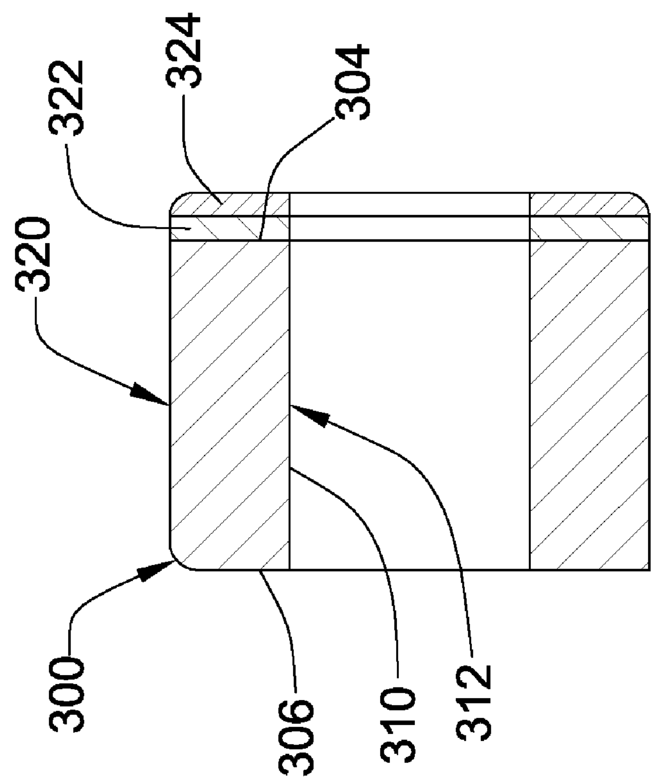
FIG. 4 is a cross-sectional view of an attachment mold, in accordance with an embodiment.

FIG. 3 is a perspective view of an attachment mold 300, in accordance with an embodiment. FIG. 4 is a cross-sectional view of the attachment mold 300 of FIG. 3 along cut-line 4-4. The attachment mold 300 comprises a mold first surface 304 and a mold second surface 306 opposite the mold first surface 304. The attachment mold 300 defines a mold bore 310 having a bore surface 312 extending from the mold first surface 304 to the mold second surface 306 therethrough. The attachment mold 300 further defines a mold perimeter surface 320 that defines a predetermined shape as will be explained below.

In accordance with an embodiment, the attachment mold 300 comprises an elastic material operable to be readily stretched and peeled from the tooth 150 and attachment device 160, shown in FIG. 2, after the curing of the curable material therein. Being elastic means that the attachment mold 300 may be worked off from the attachment device 160 within it, and/or the attachment mold 300 may be cut or torn to be removed from the attachment device 160.

The attachment mold 300 further comprises an adhesive layer 324 on the mold first surface 304. The adhesive layer 324 is operable for removably coupling the attachment mold 300 to a tooth surface 154.

Figure 5:
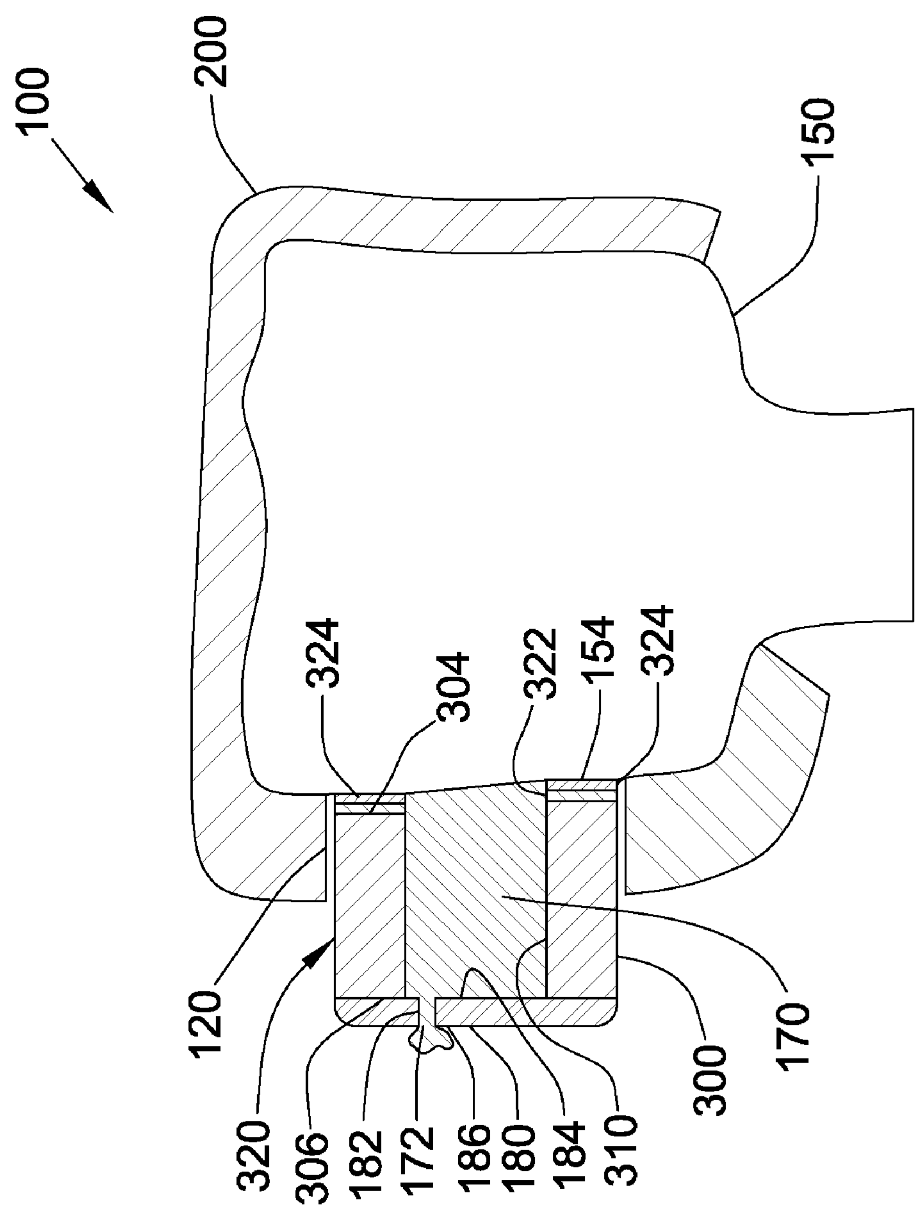
FIG. 5 is a cross-sectional view of a system for forming and coupling one or more attachment devices onto one or more teeth as coupled to a tooth, in accordance with an embodiment.

FIG. 5 is a cross-sectional view along cut-line 5-5 shown in FIG. 1 of an embodiment of a system 100 as disposed onto a tooth 150 with the addition of curable material 170 and the cover plate 180, in accordance with an embodiment. In accordance with an embodiment, the adhesive layer 324 provides a means to conform the mold first surface 304 to an irregular tooth surface 154. The adhesive layer 324 may allow for conformance of the mold first surface 304 to the irregular tooth surface 154 by one or more of any suitable means, such as, but not limited, the elastic properties of the adhesive layer 324, pressure-sensitivity of the adhesive layer 324, a foam matrix within the adhesive layer 324, and/or in combination with the resiliency and elasticity of the attachment mold 300, among many others.

In accordance with an embodiment, the adhesive layer 324 provides a sealing engagement with the tooth surface 154 so as to resist the infiltration of saliva or other contaminants onto the tooth surface 154 exposed by the mold bore 310. In accordance with an embodiment, the adhesive layer 324 resists the migration between the mold first surface 304 and the tooth surface 154 of curable material 170 that is disposed within the mold bore 310 prior to curing the curable material 170 forming the attachment device 160 that is coupled to the tooth surface 154. Further, in accordance with an embodiment, the adhesive layer 324 resists the migration between the mold first surface 304 and the tooth surface 154 of tooth surface preparation materials and solutions, such as, but not limited to, etching and cleaning solutions.

In accordance with an embodiment, the adhesive layer 324 comprises a material which is opaque to those light frequencies associated with curing curable material which is curable by exposure to light-curing radiation. The opaque adhesive layer 324 is operable to shadow or block light-curing radiation from illuminating between the mold first surface 304 and the tooth surface 154 and therefore resists the curing of any curable material 170 that may unintentionally migrate between the mold first surface 304 and the tooth surface 154 resulting in flash. Any uncured curable material 170 left on the tooth surface 154 after removal of the attachment mold 300 may be removed relatively easily as compared with flash that is cured.

In accordance with an embodiment, the adhesive layer 324 comprises a material which is operable to removably couple to the tooth surface 154 to the extent that it restricts liquids and gels from penetrating between it and the tooth surface 154. The adhesive layer 324 is operable to be peeled off or otherwise removed from the tooth surface 154 after use without altering or damaging the tooth surface 154 or contour thereof.

In accordance with an embodiment, the adhesive layer 324 is operable to resist decoupling of the attachment mold 300 from the tooth surface 154 which may be facilitated by any surface preparation of the exposed tooth surface 154, such as, but not limited to, by cleaning, etching, and drying, that may occur prior to the deposition of the curable material 170 into the mold bore 310. This provides, among other things, for a very limited area of exposure of the tooth surface 154 to chemical and mechanical surface preparation that may affect the tooth surface 154 to only that location associated with an attachment device.

In accordance with another embodiment, an opaque layer 322 comprising a material which is opaque to those light frequencies associated with curable material which is curable by exposure to light-curing radiation is disposed between the mold first surface 304 and the adhesive layer 324, as shown in FIG. 4. The opaque layer 322 is operable to shadow or block light-curing radiation from illuminating between the mold first surface 304 and the tooth surface 154 and therefore resists the curing of any curable material 170 that may unintentionally migrate between the mold first surface 304 and the tooth surface 154. Any uncured curable material left on the tooth surface 154 after removal of the attachment mold 300 may be removed relatively easily as compared with flash that is cured.

It is appreciated that the attachment mold 300 may itself comprise an opaque material operable to block the light-curing radiation from illuminating between the mold first surface 304 and the tooth surface 154. But it is also appreciated that the illumination of light-curable material 170 may be assisted wherein the attachment mold 300 comprises a transparent material operable to allow light-curing radiation to illuminate the curable material 170 within the mold bore 310 from the top as well as from the sides of the attachment mold 300.

Figure 6:
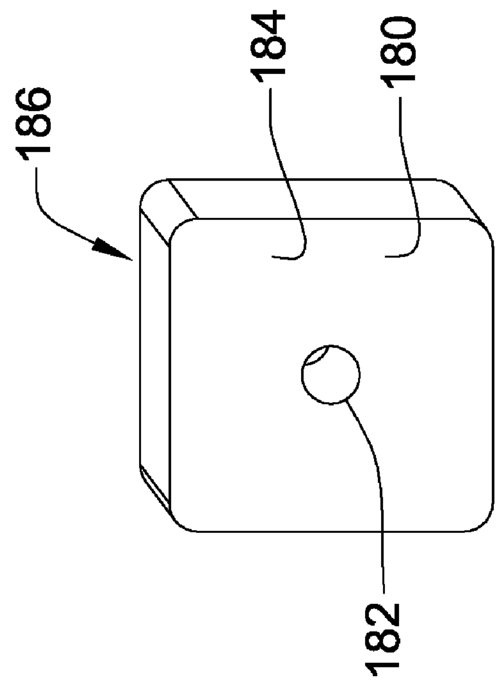
FIG. 6 is a perspective view of a cover plate including a plate aperture in accordance with an embodiment.

FIG. 6 is a perspective view of a cover plate 180 including a plate aperture 182 in accordance with an embodiment. The cover plate 180 comprises a plate inner surface 184 and a plate outer surface 186 opposite the plate inner surface 184. The plate aperture 182 extends from the plate inner surface 184 to the plate outer surface 186 therethrough. In accordance with an embodiment, the cover plate 180 is substantially flat. The cover plate 180 is operable to cover the mold bore 310 and the mold second surface 306. Wherein a light-curable curable material is used to form an attachment device, the cover plate 180 may comprise a material that is translucent to light-curing radiation.

The cover plate 180 is operable for allowing for the compression of curable material 170 within the mold bore 310 to affect intimate contact between the curable material 170 and the tooth surface 154 and minimize voids within the curable material 170. The plate aperture 182 is operable for allowing excess curable material 170 to extrude from the mold bore 310 under pressure created as the cover plate 180 is pressed against the mold second surface 306 and curable material 170, such as shown in FIG. 5.

It is appreciated that in another embodiment, the cover plate 180 may be provided without a plate aperture 182, wherein any excess curable material 170 may extrude around the edges of the cover plate 180 under pressure created as the cover plate 180 is pressed against the mold second surface 306 and curable material 170.

In accordance with an embodiment, each of the attachment molds 300 has one of a predetermined unique shape of the mold perimeter surface 320 that is complementary with a predetermined unique shape of a corresponding aperture perimeter 212 of the aperture 210 in the template 200. The unique shape of the mold perimeter surface 320, among other things, prevents the use of an attachment mold 300 that was not intended for the attempted location on the template 200. An attachment mold 300 that is mismatched to an aperture 210 will not fit properly within the aperture 210 preventing advancement of the attachment mold 300 to the tooth surface 154. The ill-fitting correspondence between the attachment mold 300 and the aperture 210 alerts the practitioner that an incorrect attachment mold 300 is being attempted at placement.

In accordance with an embodiment, a particular unique size and/or shape of the mold perimeter surface 320 may be associated with a particular unique size and/or shape of an attachment mold bore 310 suitable for forming an attachment device 160 of a unique size and/or shape. FIGS. 7A-7C are top views of embodiments of various attachment molds 300*a-c* by way of example and not limited thereto. In FIG. 7*a*, a first attachment mold 300*a* comprises a particular shape of a first mold perimeter surface 320*a* and a first mold bore 310*a* having a rectangular cross-section that is operable to produce an attachment device in the form of a post having a rectangular cross-section. In FIG. 7*b*, a second attachment mold 300*b* comprises a second mold perimeter surface 320*b* having a triangular-shaped cross-section and a second mold bore 310*b* having a square cross-section that is operable to produce an attachment device in the form of a post having a square cross-section. In FIG. 7*c*, a third attachment mold 300*c* comprises a third mold perimeter surface 320*c* having an octagonal-shaped cross-section and a third mold bore 310*c* having a triangular cross-section that is operable to produce an attachment device in the form of a post having a triangular cross-section. Again, the uniqueness of the size and/or shape of the mold parameter surface 320 having a particular size and/or shape of mold bore 310, among other things, alerts the practitioner that a correct or incorrect attachment mold 300 is being attempted at placement at a particular template aperture 210*t*.

Figure 8:
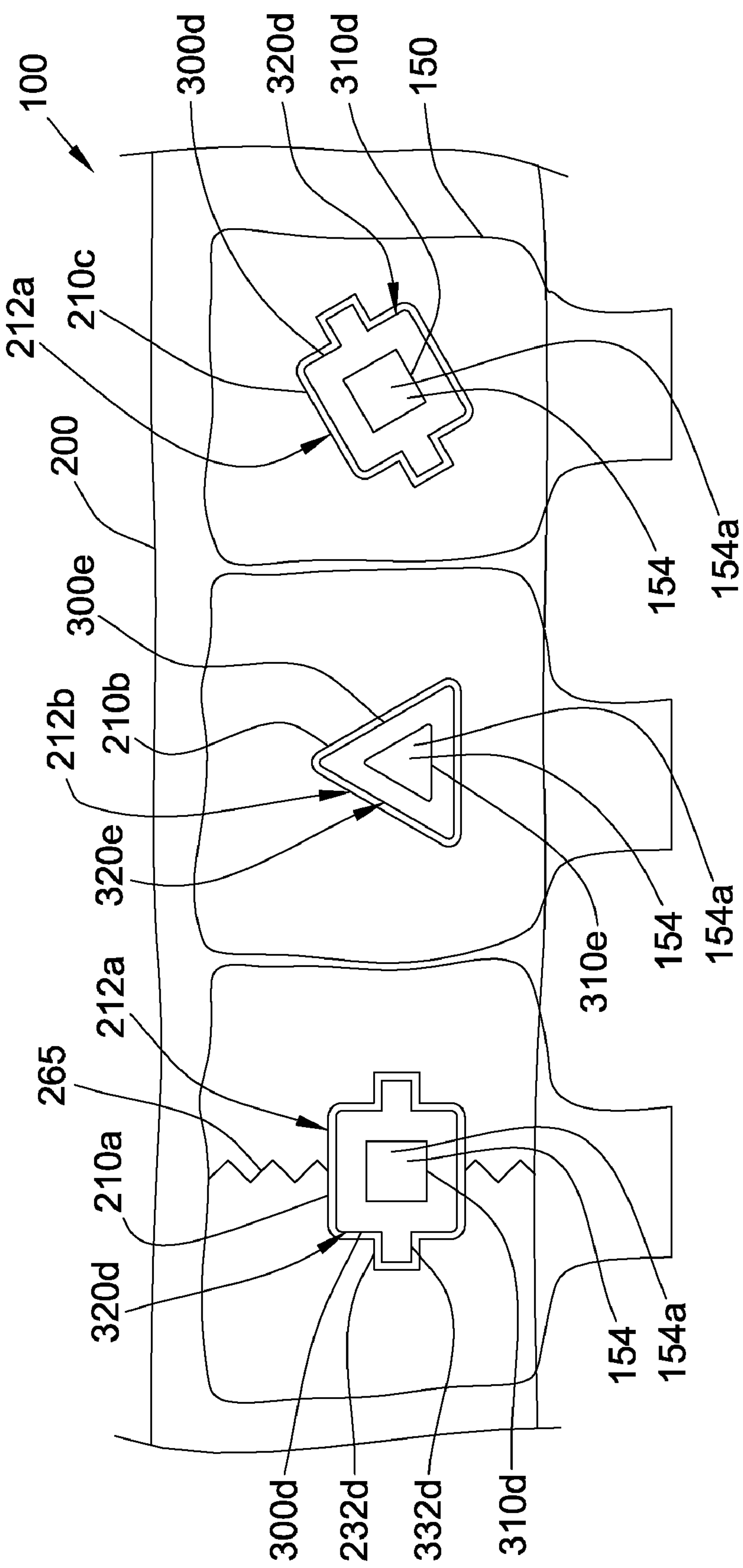
FIG. 8 is a side view of various attachment molds as coupled to teeth through a template, in accordance with embodiments.

FIG. 8 is a partial side view of a system 100 showing teeth 150, a template 200, and attachment molds 300 coupled to the teeth 150, in accordance with an embodiment. The template 200 has a first aperture 210*a* with a first aperture perimeter 212*a*, a second aperture 210*b* having a second aperture perimeter 212*b*, and a third aperture 210*c* having a first aperture perimeter 212*a*. The first aperture 210*a* and the third aperture 210*c* have the same aperture perimeter 212*a* but at different orientations to the respective tooth surface. The first aperture 210*a* and the third aperture 210*c* are operable to receive a first attachment mold 300*d* having a fourth mold perimeter surface 320*d* and a fourth mold bore 310*d* exposing a portion of the tooth surface 154. The second aperture 210*b* is operable to receive a fifth attachment mold 300*e* having a fifth mold perimeter surface 320*e* and a fifth mold bore 310*e* exposing a portion of the tooth surface 154.

By way of example, the unique aperture perimeter 212*a* provides, among other things, a keyway 232*d* that is operable to cooperate with the corresponding mold perimeter surface 320 including keys 332*d*, ensuring, among other things, the use of the proper mold 300*d* and/or the proper orientation of the mold 300*d* within the aperture 210*a*. Where the attachment mold 300*d* may be received within the aperture 210*a* in only a predetermined orientation assures that the attachment mold 300*d* is correctly orientated to the tooth surface 154 substantially where prescribed.

By way of example, but not limited thereto, a system 100 is described as suitable for a particular patient. Measurement data of a patient's teeth is collected. Measurement data may be collected by one of any suitable processes, such as, but not limited to, creating a physical impression of the patient's teeth 150 and creating a virtual impression of the patient's teeth 150 via a process such as, but not limited to, computer scanning. An impression, or a virtual, computer-generated "impression", of the patient's teeth 150 is created. A computer model of the patient's teeth 150 is created based on the measurement data using processes known in the art, such as those described in Chishti et al., U.S. Pat. No. 5,975,893, incorporated herein by reference.

The design of the template 200 is facilitated by computer-aided design methodologies known in the art, such as those provided in Chishti et al. in U.S. Pat. No. 5,975,893. A computer model of the patient's teeth and the desired result of the positions of the teeth is analyzed to determine whether the use of attachment devices 160 would aid in the desired movement of the teeth 150 from a first position to a second position. The use of attachment devices 160 of particular geometries may provide movement of the teeth 150 that is more efficient or along a different path than achievable based on relying entirely on force bearing natural tooth surfaces or contours of the teeth 150. The location and shape of attachment devices 160 at specific locations of the teeth 150, as well as which specific shape of attachment device 160 that is appropriate for the intended purpose, are determined.

A template 200 is created that is operable to engage and removably couple onto one or more of the teeth 150 in substantially the same manner as a positioning appliance as described in Chishti et al. The template 200 is provided with apertures 210 corresponding to those locations that analysis had determined an attachment device 160 is to be provided on the teeth 150. Each aperture 210 defines a unique shape of the aperture perimeter 212, in accordance with an embodiment, or one of a finite set of shapes of aperture perimeters 212 in accordance with another embodiment.

Attachment molds 300 are provided, one of each having a unique shape of the mold perimeter surface 320 corresponding to one of each aperture 210 having a unique shape of the aperture perimeter 212 provided in the template 200. Each of the attachment molds 300 defines a mold bore 310 suitable for providing a mold for forming an attachment device 160 of the desired shape from curable material 170 suitable for a particular purpose. Since each aperture 210 and corresponding attachment mold 300 has one of a unique shape of aperture perimeter 212 and mold perimeter surface 320, respectively, that are complementary to each other such that a respective attachment mold 300 may be received within a corresponding aperture 210, a practitioner cannot place an incorrect attachment mold 300 in a given aperture 210.

It is understood that the modularity of the association of apertures 210 and attachment molds 300 allows for many combinations wherein unique and/or similar attachment molds 300 may be used in a given aperture 210. By way of example but not limited there to, a plurality of attachment molds 300 having the same shape of mold perimeter surface 320 and same shape of the mold bore 310 may be used interchangeably within multiple apertures 210 to provide an attachment device 160 of a given same shape. The orientation of the attachment device 160 may be determined by the orientation of the aperture 210 relative to the tooth surface 154 that is exposed by the aperture 210, such as shown in FIG. 8.

In accordance with embodiments of methods, the template 200 is placed over the teeth 150. Each aperture 210 allows access to the tooth surface 154 at the locations wherein an attachment device 160 is to be formed and coupled to the tooth surface 154. A plurality of attachments molds 300 are provided, each having one of a unique shape of mold perimeter surface 320*d,e* corresponding to each of the corresponding apertures 210*a-c* each having one of a corresponding shape of the aperture perimeter 212*a,b*. An attachment mold 300 is coupled to the tooth surface 154 through the aperture 210*a-c*. The tooth surface 154 that is exposed by the mold bore 310*d,e* is prepared to receive an attachment device 160.

In accordance with an embodiment, each of the attachment molds 300 has one of a predetermined unique cross-section of the mold bore 310 so as to produce an attachment device 160 having a unique cross-section. In accordance with other embodiments, multiple attachment molds 300 having one of a finite set of unique cross-sections of mold bores 310 is provided.

The bore 310 of the attachment mold 300 determines, in part, the resulting shape of the attachment device 160. The shape of the bore 310 may be any suitable shape that is operable to be molded. By way of example, the bore 310 may have a square lateral cross-section that results in an attachment device 160 having a square lateral cross-section having a height substantially corresponding to the distance between the mold first surface 304 and the mold second surface 306.

The shape of the attachment device 160 is predetermined based, in part, on the prescribed force desired for that specific location in order to transmit force generated by the dental positioning appliance to the teeth 150.

In accordance with an embodiment, the attachment devices 160 may be relatively small, for example, but not limited to, 2 mm wide by 4 mm long by 2 mm high, as compared with conventional dental brackets. The prescribed size and shape of the attachment devices 160 may vary in order to provide ideal function as prescribed during treatment plan development.

The attachment devices 160 may be coupled at specific locations throughout the dentition where appropriate and this may only be required at one or a few locations. The attachment devices 160 may be coupled to any surface of the teeth 150, including lingual surfaces.

In accordance with embodiments, the attachment devices 160 may provide the function of one or more of, but not limited to, an anchor for the removable coupling of the positioning appliance to the teeth, and as a point of leverage for the positioning appliance to exert a prescribed force onto the teeth.

Again, FIG. 5 is a cross-sectional view of an embodiment of the template 200 and the attachment mold 300 operable for forming and coupling one or more attachment devices onto one or more teeth 150. The template 200 is disposed onto and is in snug removable engagement with the teeth 150. An aperture 120 exposes a portion of the tooth surface 154 onto which an attachment device is to be formed and coupled to the tooth surface 154. An attachment mold 300 is disposed within the aperture 120 with the adhesive layer 324 coupling the attachment mold 300 to the tooth surface 154. The mold bore 310 defines a portion of the tooth surface 154 as the target tooth surface 154*a*. The target tooth surface 154*a* is prepared to receive the curable material 170. Curable material 170 is disposed within the mold bore 310 and in contact with the target tooth surface 154*a*. A cover plate 180 is disposed over the mold second surface 306 with any excess curable material 172 allowed to extrude from the plate inner surface 184 to the plate outer surface 186 through the plate aperture 182. Excess curable material 172 which has extruded from the plate aperture 182 and/or from around the edge of the cover plate 180 may be removed prior to curing the curable material 170.

The curable material 170 is cured into a hardened state forming the attachment device 160 that is coupled to the tooth surface 154. FIG. 9 is a side view of the attachment device 160 as coupled to the tooth 150, in accordance with an embodiment. The attachment mold 300 is removed from the attachment device 160. The template 200 may be removed intact and reused for forming subsequent attachment devices 160 or may be divided into various pieces so as to be more easily removed from the teeth 150. Any remaining flash of cured curable material 172 on the top surface of the attachment device 160, such as that from within the plate aperture 182, is relatively easily removed, such as, but not limited to, by mechanical grinding and the like. Any resulting flash of uncured curable material 172 that may be present around the base of the attachment device 160 from between the mold first surface 304 and the tooth surface 154 may be removed by wiping and/or washing.

Figure 10A:
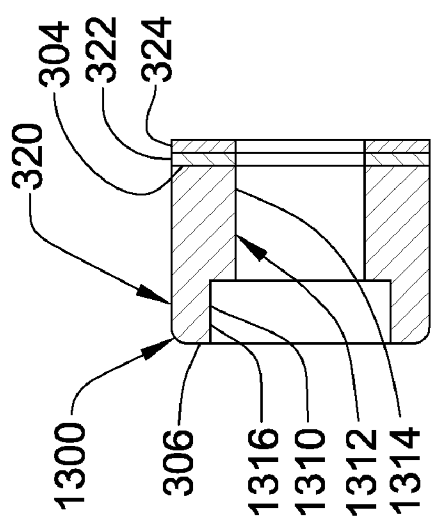
FIG. 10A is a side cross-sectional view of an attachment mold in accordance with another embodiment.
Figure 10B:
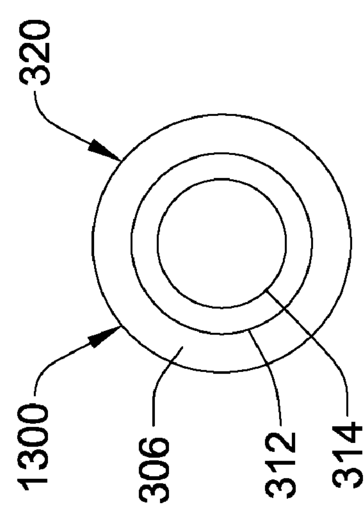
FIG. 10B is a top view of the attachment mold in accordance with the embodiment of FIG. 10A.

It is appreciated that the attachment mold may comprise a mold bore having a shape suitable to a particular purpose. FIGS. 10A and 10B are cross-sectional and top views, respectively, of an attachment mold 1300 in accordance with another embodiment. The attachment mold 1300 comprises a mold first surface 304 and a mold second surface 306 opposite the mold first surface 304. The attachment mold 1300 defines a mold bore 1310 having a bore surface 1312 extending from the mold first surface 304 to the mold second surface 306 therethrough. The mold bore 1310 comprises a first portion 1314 having a first diameter and a second portion 1316 having a second diameter that is larger than the first portion 1314. The mold bore 1310 has a compound circular cross-section that is operable to produce an attachment device in the form of a cylindrical post having two diameters. The attachment mold 1300 further comprises an opaque layer 322 and an adhesive layer 324 on the mold first surface 304. The adhesive layer 324 is operable for removably coupling the attachment mold 1300 to a tooth surface 154.

Figure 11:
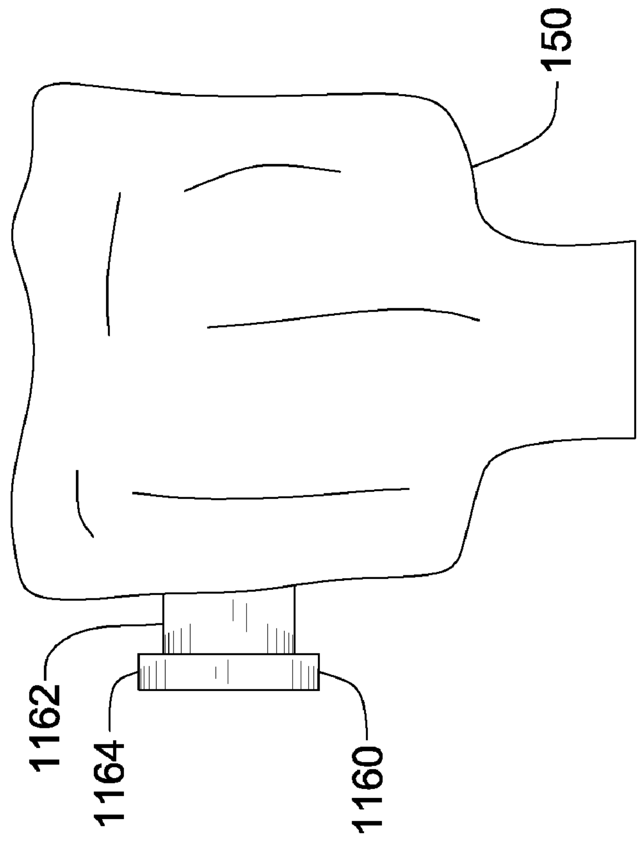
FIG. 11 is a side view of another attachment device as coupled to the tooth, in accordance with another embodiment.

FIG. 11 is a side view of a compound attachment device 1160 that may be formed by the attachment mold 1300 of FIGS. 10A,B. The compound attachment device 1160 comprises a top 1164 that is coupled to the tooth 150 by a shaft 1162 having a reduced diameter than that of the top 1164. The mold bore 1310, as shown in FIGS. 10A,B, is operable to accept curable material therein so as to simultaneously form the top 1164 and the shaft 1162 of the attachment device 1160 that is coupled to the tooth 150 when cured.

The compound attachment device 1160 may or may not be used in association with positioning appliances. The compound attachment device 1160 may be particularly suitable for providing an anchor or an engagement for other dental devices, such as, but not limited to, orthodontic wires and elastic bands.

Figure 12:
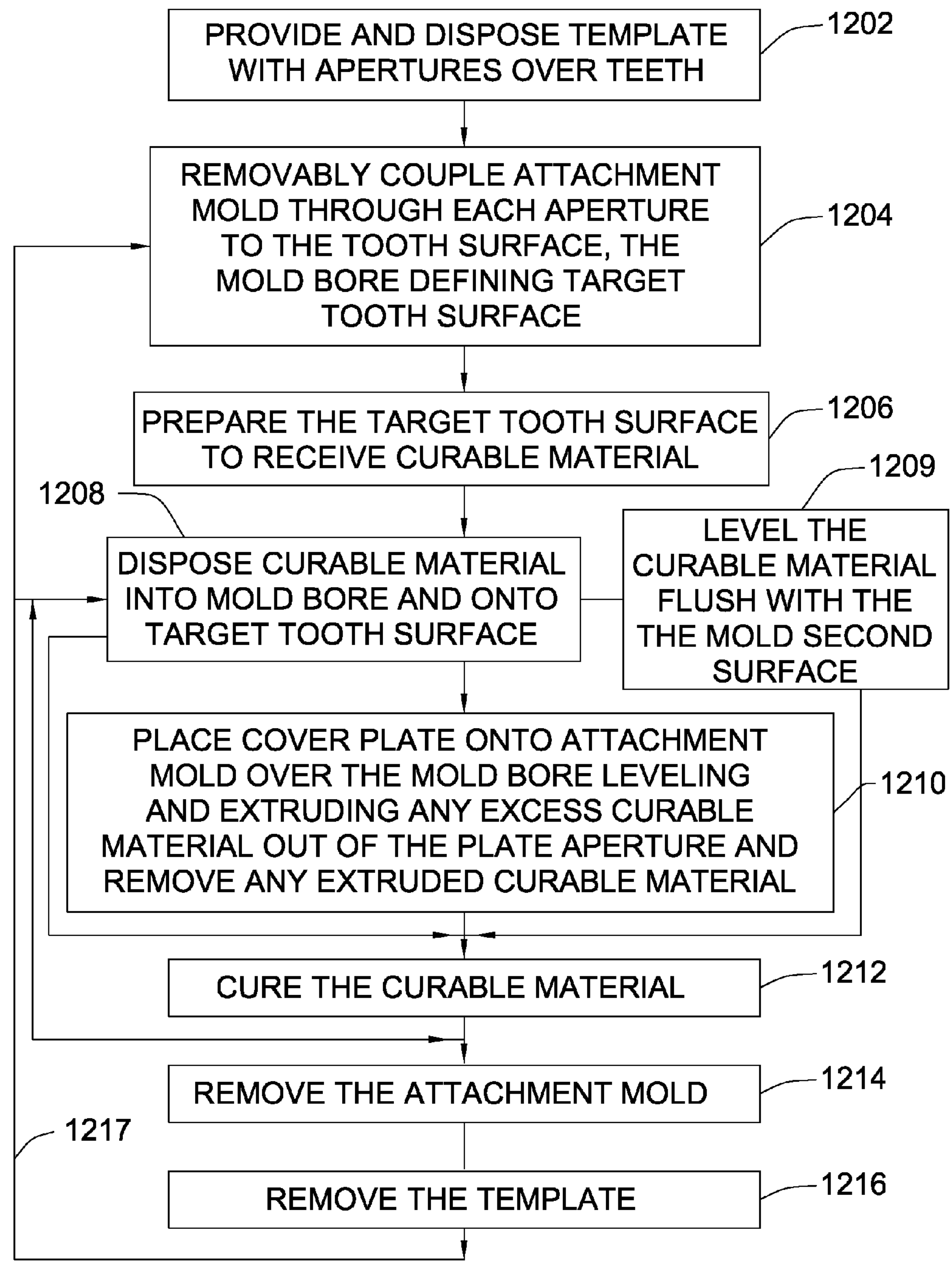
FIG. 12 is a flow chart of methods in accordance with embodiments.

FIG. 12 is a flow chart of a method in accordance with an embodiment. A template comprising a prescribed number and placement of apertures is provided and placed over the teeth exposing tooth surface through each aperture 1202. A predetermined attachment mold is provided and received within each respective aperture and removably coupled to the tooth surface, the mold bore defining target tooth surface 1204. The target tooth surface is suitably prepared to receive curable material 1206, such as, but not limited to, cleaned, etched, rinsed, dried, and treated with bonding agent. Curable material is disposed within the mold bore of the attachment mold and in contact with the target tooth surface 1208. In an embodiment, the curable material is made level with the mold second surface of the attachment mold 1209. In accordance with another embodiment, a cover plate with a plate aperture is disposed on the mold second surface and over the mold bore extruding any excess curable material through the plate aperture, with any excess curable material being removed from the cover plate 1210. The curable material is cured to a hardened state to form an attachment device that is coupled to the target tooth surface 1212. The attachment mold is removed from the attachment device and the template 1214. Additional attachment devices are formed by repeating the process with the other predetermined attachment molds received within respective apertures 1217. The template is removed from the teeth 1216.

In accordance with another embodiment, the method of FIG. 12 further comprises preparing the surface of the teeth to couple with the adhesive on the mold first surface before placement of the template. The surface of the teeth is prepared to provide a suitable coupling surface for the adhesive by, such as, but not limited to, cleaning, removal of tarter and plaque, drying, and treating with a bonding agent. Substantially the same preparation activities may be suitable for preparing the target tooth surface for receiving curable material to affect a good coupling between the tooth surface and the resulting attachment device.

In accordance with embodiments, the template 200 may comprise means, such as, but not limited to, frangible portions 265 as shown in FIG. 8, to provide for easily breaking apart, particularly at the apertures, so as to facilitate removal of the template from the teeth and attachment devices.

In accordance with embodiments, the attachment mold 300 may comprise means, such as, but not limited to, frangible portions and elastic properties, to provide for easily breaking apart, peeling away, or elastically deforming, so as to facilitate removal of the attachment mold 300 from the attachment device 160.

The curable material may be cured by any process suitable for the particular material. By way of example, but not limited thereto, light-curable composite resin used for dental applications may be suitable for the particular purpose. Many curable materials are known in the art and it is appreciated that the materials are cured in the manner that the particular material is formulated to be cured.

In accordance with another embodiment of a method, the attachment molds 300 are disposed within respective apertures 210 and removably coupled to the template 200 prior to the placement of the template 200 onto the teeth 150. The attachment molds 300 are held within the respective aperture 210 and recessed from the template inner surface 204, and therefore recessed from the tooth surface 154 upon placement of the template 200 onto the teeth 150. Once the template 200 is seated onto the teeth 150, the attachment molds 300 are released from the template 200 and pressed against the tooth surface 154.

A single placement system for forming and coupling an attachment device onto a tooth is provided in accordance with another embodiment. The single placement system is substantially the same as the various embodiments of system 100 discussed above but without the template 200. The single placement system may be particularly useful where precise placement of an attachment device is not critical to the use of the attachment device. By way of example, but not limited thereto, the attachment device 1160 of FIG. 11 may be particularly useful to provide a feature to hook an elastic band to, such may be used to erupt teeth or to grossly rotate them. Precise location and orientation of the attachment device may not be critical to these uses. In contrast to bonding a preformed attachment device to the tooth, an attachment device may be simultaneously formed and coupled to the tooth with the single placement system.

The single placement system comprises one or more attachment molds. The attachment molds are substantially the same as the embodiments of attachment mold 300 of FIG. 4, the attachment molds **300*d*,300*e* of FIG. 8, and the attachment mold 1300 of FIG. 10A. The uniqueness of the mold perimeter, such as the key 332*d* shown in FIG. 8, is not critical for the single placement system since a template is not used. The attachment mold further comprises an opaque layer 322 and an adhesive layer 324 on the mold first surface 304 such as provided in FIG. 4. The adhesive layer 324 is operable for removably coupling the attachment mold 300 to a tooth surface 154**.

A method for forming and coupling an attachment device onto a tooth using the single placement system is substantially the same as the method for using system 100 as provided in FIG. 12, but without the use of the template. In accordance with an embodiment, a predetermined attachment mold is removably coupled to the tooth surface, with the mold bore defining target tooth surface. The mold first surface of each attachment mold is removably coupled to the exposed tooth surface with the mold bore defining target tooth surface through each mold bore. The target tooth surface is suitably prepared to receive curable material, such as, but not limited to, cleaned, etched, rinsed, dried, and treated with bonding agent. Curable material is disposed within the mold bore of the attachment mold and in contact with the target tooth surface. In an embodiment, the curable material is made level with the mold second surface of the attachment mold. In accordance with another embodiment, a cover plate with a plate aperture is disposed on the mold second surface and over the mold bore extruding any excess curable material through the plate aperture, with any excess curable material being removed from the cover plate. The curable material is cured to a hardened state to form an attachment device. The attachment mold is removed from the attachment device. Additional attachment devices may be formed by repeating the process.

In accordance with another embodiment, the method further comprises preparing the surface of the tooth to couple with the adhesive on the mold first surface before placement of the mold onto the tooth. The surface of the tooth is prepared to provide a suitable coupling surface for the adhesive by, such as, but not limited to, cleaning, removal of tarter and plaque, drying, and treating with a bonding agent. Substantially the same preparation activities may be suitable for preparing the target tooth surface for receiving curable material to affect a good coupling between the tooth surface and the resulting attachment device.

The attachment devices 160 in combination with removable dental positioning appliances provide the patient with the benefits of removable appliances while enhancing the ability of those appliances to extrude, rotate, and otherwise manipulate teeth as is done with conventional braces. Embodiments provided herein provide a system that enables precise placement of an attachment device on a dental surface for a patient undergoing orthodontic repositioning.

Embodiments provided herein are directed to simultaneously forming and coupling attachment devices to dental surfaces suitable for cooperative engagement with positioning appliances. The cooperative engagement may be, but not limited to, assist in the retention of the positioning appliance on the teeth and for the more efficient transmission of force(s) from the positioning appliance to the teeth. Embodiments herein allow for, among other things, the accurate placement of the attachment devices, the prevention of flashing of the curable material, the precise dimensionality of the attachment devices, the use of curable material having desired viscosities or other material properties that are not dependent on the handling concerns of the template, and allowing the serial processing of forming multiple attachments, among other things.

While the invention has been described in connection with specific embodiments thereof, it will be understood that it is capable of further modification, and this application is intended to cover any variations, uses, or adaptations of the invention following, in general, the principles of the invention and including such departures from the present disclosure as come within known or customary practice in the art to which the invention pertains and as may be applied to the essential features hereinbefore set forth, and as fall within the scope of the invention and the limits of the appended claims.

I claim:

1. A system for forming and coupling an attachment device onto one or more teeth, comprising:

a template comprising a shell having a cavity defining a shape for receiving one or more teeth, the template including a template inner surface and a template outer surface opposite the template inner surface, the template further comprising an aperture at one or more predetermined locations that extends from the template inner surface to the template outer surface therethrough, the aperture defining an aperture perimeter;

one or more attachment molds, each attachment mold comprising a mold first surface and a mold second surface opposite the mold first surface, the attachment mold includes a mold bore having a bore surface extending from the mold first surface to the mold second surface therethrough, the attachment mold further includes a mold perimeter surface that defines a predetermined shape, wherein each of the aperture perimeters being operable to receive and cooperate with the mold perimeter surface of one of the attachment molds;

an adhesive layer disposed on the mold first surface for removably coupling the attachment mold to a tooth surface with the mold bore defining a portion of the tooth surface as target tooth surface;

curable material disposed within and filling the mold bore from the mold first surface and the target tooth surface to the mold second surface that will be the attachment device, wherein each mold bore provides a mold for forming an attachment device of a desired shape and orientation from the curable material, the adhesive layer being enabled to provide a sealing engagement with the tooth surface that substantially prevents the curable material from migrating away from the target tooth surface between the mold first surface and the tooth surface; and a cover plate including a plate inner surface and a plate outer surface opposite the plate inner surface, the cover plate being operable to be placed upon the mold second surface and cover the mold bore, the cover plate being operable for the compression of curable material that may be within the mold bore to affect intimate contact between the curable material and the target tooth surface and minimize voids within the curable material, the cover plate comprising a material that is translucent to those light frequencies associated with curable material which is curable by exposure to light-curing radiation.

2. The system of claim 1, wherein the adhesive layer provides a means to conform the mold first surface to an irregular tooth surface upon which it may be removably coupled.

3. The system of claim 2, wherein the means to conform the mold first surface is selected from a list consisting of: elastic properties of the adhesive layer; pressure-sensitivity of the adhesive layer; a foam matrix within the adhesive layer; the resiliency of the attachment mold; and combinations thereof.

4. The system of claim 2, wherein the adhesive layer provides a sealing engagement with the tooth surface so as to resist the infiltration of contaminants between the mold first surface and the tooth surface.

5. The system of claim 2, wherein the adhesive layer resists the migration of curable material away from the target tooth surface between the mold first surface and the tooth surface that may be disposed within the mold bore and on the target tooth surface prior to curing the curable material forming an attachment device.

6. The system of claim 2, wherein the adhesive layer is opaque to those light frequencies associated with curing curable material which is curable by exposure to light-curing radiation, wherein the adhesive layer blocks light-curing radiation from illuminating between the mold first surface and the tooth surface and therefore resists the curing of any curable material that may unintentionally migrate between the mold first surface and the tooth surface.

7. The system of claim 2, wherein the attachment mold further comprises an opaque layer disposed between the mold first surface and the adhesive layer, the opaque layer comprising a material which is opaque to those light frequencies associated with curable material which is curable by exposure to light-curing radiation, wherein the opaque layer substantially blocks light-curing radiation from illuminating under the attachment mold and therefore resist the curing of any curable material that may unintentionally migrate between the mold first surface and the tooth surface.

8. The system of claim 2, wherein the attachment mold comprises an opaque material for blocking light-curing radiation from illuminating between the mold first surface and the tooth surface when coupled to the tooth surface.

9. The system of claim 2, wherein the attachment mold comprises a transparent material so as to allow light-curing radiation to illuminate curable material that may be within the mold bore through the attachment mold.

10. The system of claim 1, the cover plate further comprising a plate aperture extending from the plate inner surface to the plate outer surface therethrough, the plate aperture being operable for allowing any excess curable material to extrude from the mold bore under pressure created as the cover plate is pressed against the mold second surface and any curable material disposed within the mold bore.

11. The system of claim 1, wherein each of the attachment molds has one of a predetermined unique shape of the mold perimeter surface that is complementary with a predetermined unique shape of a corresponding aperture perimeter, wherein the unique shape of the mold perimeter surface prevents the use of an attachment mold that may not be intended for an attempted location defined by the aperture on the template.

12. The system of claim 11, wherein the predetermined unique shape of a corresponding aperture perimeter defines a keyway for a corresponding mold perimeter surface identifying a complementary predetermined unique shape for receiving the keyway.

13. The system of claim 11, wherein a predetermined unique shape of the mold perimeter surface is associated with a predetermined unique shape of an attachment mold bore.

14. The system of claim 1, wherein the mold bore comprises a first portion adjacent the mold first surface having a first diameter and a second portion adjacent the mold second surface having a second diameter that is larger than the first portion.

15. The system of claim 1, wherein the template comprises frangible portions to facilitate removal of the template from the teeth and any attachment devices.

16. The system of claim 1, wherein the attachment mold is provided with means to facilitate removal of the attachment mold from an attachment device.

17. The system of claim 1, wherein the attachment mold comprises an elastic material wherein the attachment mold may be readily stretched and peeled from the tooth and attachment device.

18. The system of claim 1, wherein the attachment molds are disposed within and removably coupled to respective apertures.

19. A system for forming and coupling an attachment device onto one or more teeth, comprising:

one or more attachment molds, each attachment mold comprising a mold first surface and a mold second surface opposite the mold first surface, the attachment mold includes a mold bore having a bore surface extending from the mold first surface to the mold second surface therethrough;

an adhesive layer disposed on the mold first surface for removably coupling the attachment mold to a tooth surface with the mold bore defining a portion of the tooth surface as target tooth surface;

curable material disposed within and filling the mold bore from the mold first surface and the target tooth surface to the mold second surface will be the attachment device that, wherein each mold bore provides a mold for forming an attachment device of a desired shape from the curable material the adhesive layer being enabled to provide a sealing engagement with the tooth surface that substantially prevents the curable material from migrating away from the target tooth surface between the mold first surface and the tooth surface; and a cover plate including a plate inner surface and a plate outer surface opposite the plate inner surface, the cover plate being operable to be placed upon the mold second surface and cover the mold bore, the cover plate being operable for the compression of curable material that may be within the mold bore to affect intimate contact between the curable material and the target tooth surface and minimize voids within the curable material, the cover plate further comprising a plate aperture extending from the plate inner surface to the plate outer surface therethrough, the plate aperture being operable for allowing any excess curable material to extrude from the mold bore under pressure created as the cover plate is pressed against the mold second surface and any curable material disposed within the mold bore.

20. The system of claim 19, wherein the adhesive layer provides a means to conform the mold first surface to an irregular tooth surface upon which it may be removably coupled.

21. The system of claim 20, wherein the attachment mold further comprises an opaque layer disposed between the mold first surface and the adhesive layer, the opaque layer comprising a material which is opaque to those light frequencies associated with curable material which is curable by exposure to light-curing radiation, wherein the opaque layer substantially blocks light-curing radiation from illuminating under the attachment mold and therefore resist the curing of any curable material that may unintentionally migrate between the mold first surface and the tooth surface.

22. The system of claim 19, wherein the mold bore comprises a first portion adjacent the mold first surface having a first diameter and a second portion adjacent the mold second surface having a second diameter that is larger than the first portion.

23. The system of claim 20, wherein the means to conform the mold first surface is selected from a list consisting of: elastic properties of the adhesive layer; pressure-sensitivity of the adhesive layer; a foam matrix within the adhesive layer; the resiliency of the attachment mold; and combinations thereof.

24. The system of claim 19, wherein the adhesive layer provides a sealing engagement with the tooth surface so as to resist the infiltration of contaminants between the mold first surface and the tooth surface.

25. The system of claim 19, wherein the adhesive layer resists the migration of curable material away from the target tooth surface between the mold first surface and the tooth surface that may be disposed within the mold bore and on the target tooth surface prior to curing the curable material forming an attachment device.

26. The system of claim 19, wherein the adhesive layer is opaque to those light frequencies associated with curing curable material which is curable by exposure to light-curing radiation, wherein the adhesive layer blocks light-curing radiation from illuminating between the mold first surface and the tooth surface and therefore resists the curing of any curable material that may unintentionally migrate between the mold first surface and the tooth surface.

27. The system of claim 19, wherein the attachment mold comprises an opaque material that blocks light-curing radiation from illuminating between the mold first surface and the tooth surface when coupled to a tooth surface.

28. The system of claim 19, wherein the attachment mold comprises a transparent material so as to allow light-curing radiation to illuminate curable material that may be within the mold bore through the attachment mold.

29. The system of claim 19, the cover plate comprising a material that is translucent to those light frequencies associated with curable material which is curable by exposure to light-curing radiation.

30. The system of claim 19, wherein the attachment mold is provided with means to facilitate removal of the attachment mold from an attachment device.

31. The system of claim 19, wherein the attachment mold comprises an elastic material operable to be readily stretched and peeled from the tooth and attachment device.

32. The system of claim 19, further comprising:

a template comprising a shell having a cavity defining a shape for receiving one or more teeth, the template including a template inner surface and a template outer surface opposite the template inner surface, the template further comprising an aperture at one or more predetermined locations that extends from the template inner surface to the template outer surface therethrough, the aperture defining an aperture perimeter, wherein the attachment mold further comprises a mold perimeter surface that defines a predetermined shape, wherein each of the aperture perimeters may receive and cooperate with the mold perimeter surface of one of the attachment molds so as to orient the mold in a predetermined orientation to the tooth surface.

33. The system of claim 32, wherein each of the attachment molds has one of a predetermined unique shape of the mold perimeter surface that is complementary with a predetermined unique shape of a corresponding aperture perimeter, wherein the unique shape of the mold perimeter surface prevents the use of an attachment mold that may not be intended for an attempted location defined by the aperture on the template.

34. The system of claim 33, wherein the predetermined unique shape of a corresponding aperture perimeter defines a keyway for a corresponding mold perimeter surface identifying a complementary predetermined unique shape to receive the keyway.

35. The system of claim 33, wherein a predetermined unique shape of the mold perimeter surface is associated with a predetermined unique shape of an attachment mold bore.

36. The system of claim 32, wherein the template comprises frangible portions to facilitate removal of the template from the teeth and any attachment devices.

37. The system of claim 33, wherein the attachment molds are disposed within and removably coupled to respective apertures.

* * * * *